(12) United States Patent
Stocchero et al.

(10) Patent No.: US 9,017,378 B2
(45) Date of Patent: Apr. 28, 2015

(54) SURGICAL THREAD COMPRISING CELLS AND METHOD OF MANUFACTURING THE THREAD

(75) Inventors: Ithamar Stocchero, Sao Paulo (BR); Erich Odermatt, Schaffhausen (CH); Lutz Funk, Sant Cugat del Vallés (ES); Volker Friedrich, Barcelona/Rubi (ES); Marta Casanovas Albalate, Barcelona (ES)

(73) Assignees: Aesculap AG (DE); B. Braun Surgical S.A. (ES); Ithamar Stocchero (BR)

( * ) Notice: Subject to any disclaimer, the term of this patent is extended or adjusted under 35 U.S.C. 154(b) by 198 days.

(21) Appl. No.: 13/378,170

(22) PCT Filed: Jun. 25, 2010

(86) PCT No.: PCT/EP2010/059091
§ 371 (c)(1),
(2), (4) Date: May 24, 2012

(87) PCT Pub. No.: WO2011/000788
PCT Pub. Date: Jan. 6, 2011

(65) Prior Publication Data
US 2012/0232588 A1    Sep. 13, 2012

Related U.S. Application Data

(60) Provisional application No. 61/221,140, filed on Jun. 29, 2009.

(30) Foreign Application Priority Data

Nov. 6, 2009  (WO) ................. PCT/EP2009/007948
Nov. 6, 2009  (WO) ................. PCT/EP2009/007950

(51) Int. Cl.
*A61B 17/04*       (2006.01)
*A61B 17/06*       (2006.01)
(Continued)

(52) U.S. Cl.
CPC . *A61B 17/06166* (2013.01); *A61B 2017/00889* (2013.01); *A61B 2017/00893* (2013.01); *A61B 2017/06028* (2013.01); *A61B 2017/06176* (2013.01); *A61L 17/005* (2013.01);
(Continued)

(58) Field of Classification Search
USPC .......... 606/228, 229, 230, 231; 428/116, 117, 428/118
See application file for complete search history.

(56) References Cited

U.S. PATENT DOCUMENTS

| | | | |
|---|---|---|---|
| 6,174,333 | B1 | 1/2001 | Kadiyala et al. |
| 2005/0182390 | A1 | 8/2005 | Shanley |

(Continued)

FOREIGN PATENT DOCUMENTS

| | | |
|---|---|---|
| EP | 1091282 A | 11/1967 |
| EP | 1 348 499 | 10/2003 |

(Continued)

OTHER PUBLICATIONS

Merriam-Webster definition of "predominantly" as accessed on May 16, 2014; http://www.merriam-webster.com/dictionary/predominantly.*

*Primary Examiner* — Jonathan W Miles
(74) *Attorney, Agent, or Firm* — DLA Piper LLP (US)

(57) ABSTRACT

A thread, in particular surgical thread includes a cell-retaining structure and cells and a method for manufacturing the thread.

20 Claims, 2 Drawing Sheets

(51) Int. Cl.
*A61L 17/00* (2006.01)
*A61L 17/14* (2006.01)
*A61L 31/00* (2006.01)
*A61B 17/00* (2006.01)

(52) U.S. Cl.
CPC .............. *A61L 17/14* (2013.01); *A61L 31/005* (2013.01); *A61L 2300/404* (2013.01); *A61L 2300/412* (2013.01); *A61L 2300/414* (2013.01); *A61L 2300/64* (2013.01)

(56) References Cited

U.S. PATENT DOCUMENTS

2006/0047312 A1* 3/2006 Garcia Olmo et al. ....... 606/228
2007/0005110 A1 1/2007 Collier et al.
2008/0046094 A1 2/2008 Han et al.
2008/0221618 A1 9/2008 Chen et al.
2008/0255611 A1* 10/2008 Hunter .......................... 606/228
2009/0012560 A1* 1/2009 Hunter et al. ................. 606/228

FOREIGN PATENT DOCUMENTS

| EP | 1 634 608 | 3/2006 |
| EP | 1 867 288 A1 | 12/2007 |
| WO | 2005/055836 | 6/2005 |
| WO | 2007/111407 | 10/2007 |
| WO | 2009/105663 A2 | 8/2009 |
| WO | 2009/132284 | 10/2009 |

* cited by examiner

SURGICAL THREAD COMPRISING CELLS AND METHOD OF MANUFACTURING THE THREAD

RELATED APPLICATIONS

This is a §371 of International Application No. PCT/EP2010/059091, with an international filing date of Jun. 25, 2010 (WO 2011/000788 A1, published Jan. 6, 2011), which is based on U.S. Patent Application No. 61/221,140, filed Jun. 29, 2009, and International Application Nos. PCT/EP2009/007950, filed Nov. 6, 2009, and PCT/EP2009/007948, filed Nov. 6, 2009, the subject matter of which is incorporated by reference.

TECHNICAL FIELD

This disclosure relates to a thread, in particular medicinal thread, comprising cells and to a method for manufacturing the thread.

BACKGROUND

Wound closure devices and methods are well known and typically include sutures, staples and tissue adhesives.

Most prevalent is the use of needles and sutures. Sutures generally provide a high tensile strength. Further, sutures are available for nearly each type of surgical procedure. In accordance, surgical sutures are typically available in a range of conventional sizes. The size of the suture used by the surgeon for any particular procedure is dependent from the type of tissue to be sutured, the relative size of the tissue structure, as well as the forces that will be applied to the suture by the approximated tissue after the surgical procedure has been completed.

Similarly, the type of sutures selected is dependent from the procedure. Non-absorbable sutures are typically used for applications such as cardiovascular surgery, vascular surgery, orthopaedic surgery, gastrointestinal surgery, and the like. Bioabsorbable sutures are typically used for applications such as plastic surgery, skin fixation and certain soft tissue approximation, and the like. A bioabsorbable suture may be used when extended tissue approximation or fixation is not required as long as the suture maintains adequate strength during the healing period, and it is desirable to replace the suture with autologous tissue such as skin or soft tissue during the healing process.

A general drawback of sutures is the dependence on the knot technique and patient-specific factors such as constitution of the tissue or skin to be treated, resulting in a certain risk of increased scar formation or dehiscence.

Further, sutures have the highest tissue reactivity. This is mainly due to the reason that sutures are "per se" recognized as foreign bodies in the body of a patient (mammal), and thus may elicit undesired inflammatory and in particular immunological responses. Such undesired responses may lead to post-operative complications which often require surgical reinterventions.

A material for suturing covered with cells that contributes in a biologically active way to wound repair is known from the EP 1 634 608 A1. However, when pulling such a material through a tissue to be treated, there is always the risk of peeling off the cells, thereby reducing the therapeutic effect of the cells and the material, respectively.

Thus, it could be helpful to provide a surgical suture material which avoids the known disadvantages. Moreover, it could also be helpful to provide a corresponding method of manufacturing.

SUMMARY

We provide surgical thread including a cell-retaining structure and cells.

We also provide a surgical filler for plastic surgery and/or reconstructive surgery that minimizes appearance of wrinkles and/or folds including the thread.

We further provide a surgical set including at least one surgical instrument and the thread.

We further yet provide a method for manufacturing the surgical thread including finishing a cell-retaining structure with cells.

DETAILED DESCRIPTION

Figure 1:
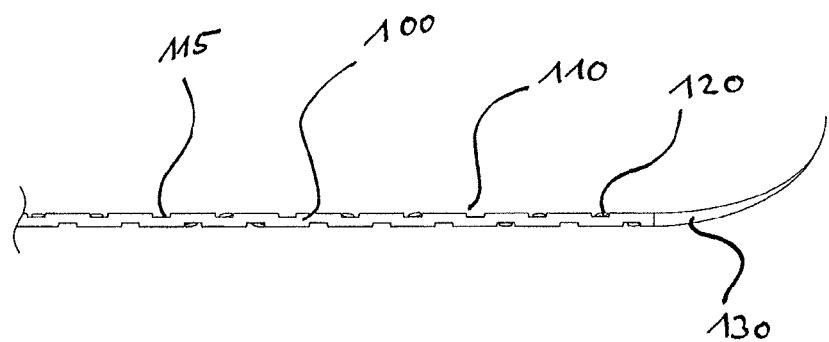
FIG. 1 schematically shows an example of a thread.

We provide a thread designed as a medical thread, more preferably as a surgical thread or surgical suture material. The thread preferably comprises a cell-retaining structure and cells. As an alternative or in combination, the thread may comprise an agent-retaining structure and agents.

The term "cell-retaining structure" as used herein is preferably understood as a structure that retains or withholds cells from becoming lost, in particular from being peeled off, during implantation or insertion of the thread into the body of a patient.

The term "agent-retaining structure" as used herein is preferably understood as a structure that retains or withholds agents from becoming lost, in particular from being peeled off, during implantation or insertion of the thread into the body of a patient.

The cell-retaining and/or agent-retaining structures advantageously allow for an effective population of cells and/or agents to be delivered to a tissue repair zone together with the thread.

Usually, the cell-retaining structure and/or agent-retaining structure are present on the surface of the thread.

In general, the cells and/or agents may partially or completely colonize or occupy, in particular coat or layer, the thread. It may be preferred that the thread is only partially colonized by the cells.

Preferably, the cells and/or agents are present on, particularly coat or layer, the surface of the thread. More specifically, the cells and/or agents may be present on an exterior surface of the thread. However, in case that the thread may be designed as a porous thread, the cells and/or agents may be present on an interior and/or exterior surface of the thread.

Especially preferably, the cell-retaining and/or agent-retaining structures comprise cell-retaining elements and/or agent-retaining elements, in particular cell-retaining loci and/or agent-retaining loci. More specifically, the cell-retaining elements and/or agent-retaining elements may be designed as cell-capturing or cell-adhering elements and/or agent-capturing or agent-adhering elements.

Advantageously, the cell-retaining elements and/or agent-retaining elements may be designed as reservoirs for the cells and/or agents. By way of example, the cell-retaining elements and/or agent-retaining elements may be selected from the group consisting of depressions, recesses, slots, fissures, openings, holes, perforations, pores and combinations thereof.

Advantageously, the cell-retaining elements and/or agent-retaining elements may have a volume to meet at least one cell and/or at least one agent, preferably a plurality, i.e., a population, of cells and/or agents.

Preferably, the cell-retaining elements and/or agent-retaining elements may have a volume of 0.02 $\mu m^3$ to 2.1 $mm^3$. Further, the cell-retaining elements and/or agent-retaining elements may have a depth of 50 $\mu m$ to 1 mm. Furthermore, the cell-retaining elements and/or agent-retaining elements may be present on the surface of the thread in a mutual distance of 100 $\mu m$ to 3 mm.

Further preferably, the cell-retaining elements and/or agent-retaining elements are designed as protuberances, i.e., as elements protruding from the surface of the thread. By way example, the protuberances may be due to a texture of the thread, which advantageously confers the thread a higher volume and, thus allows for a better capturing and adhering of the cells and/or agents.

Further, the cell-retaining elements and/or agent-retaining elements may be designed as fibers or portions thereof. More specifically, the cell-retaining elements and/or agent-retaining elements may be derived from fibers which contribute to the textile structure of the thread. For example, the cell-retaining elements and/or agent-retaining elements may be present as fibers which are cut out of the thread.

The cell-retaining structure and/or agent-retaining structure of the thread may comprise protuberances and depressions. By way of example, protuberances and depressions may be present in an alternate disposition onto the thread.

The cell-retaining elements and/or agent-retaining elements may be present as erectable protuberances which rest against the surface of the thread. Thus, the protuberances may be erected, by way of example manually or by subjecting to external stimuli, thereby advantageously allowing for a directed cellular finishing and/or agent finishing of the thread under the protuberances.

Advantageously, the cell-retaining elements and/or agent-retaining elements may also serve as anchoring means for anchoring the thread in biological tissues, particularly in human and/or animal tissues. In other words, the thread may be designed as a self-anchoring or knotless thread.

Generally, the cell-retaining elements and/or agent-retaining elements may be present in different shapes and geometries. By way of example, the cell-retaining elements and/or agent-retaining elements may be escutcheon-shaped, shield-shaped, scale-shaped, wedge-shaped, thorn-shaped, arrow-shaped, spike-shaped, twin-shaped, V-shaped, W-shaped, and combinations thereof. Further, the cell-retaining elements and/or agent-retaining elements are preferably pointed or tapered at their free ends. Furthermore, the cell-retaining elements and/or agent-retaining elements may have a multi-tip configuration, in particular a twin-tip configuration. An example for cell-retaining elements and/or agent-retaining elements having a twin-tip configuration is the above mentioned W-shaped formation of cell-retaining elements and/or agent-retaining elements. Cell-retaining elements and/or agent-retaining elements having a twin-tip configuration may in particular be based on flat cuts into the thread, preferably formed with a small angular offset and in small intervals from each other.

Furthermore, the cell-retaining elements and/or agent-retaining elements may be arranged in different dispositions on the surface of the thread. More specifically, the cell-retaining elements and/or agent-retaining elements may have a disposition onto the thread that is selected from the group consisting of a row disposition, a staggered disposition, an overlapping disposition, an offset disposition, an offset and partially overlapping disposition, a zigzag disposition, random or arbitrary disposition, a meander-like disposition, a serpentine-like disposition, a sinus-like disposition, a spiral disposition, a helical disposition, and combinations thereof.

Further, the cell-retaining elements and/or agent-retaining elements may be unidirectionally or multidirectionally, in particular bidirectionally, arranged on the surface of the thread.

Further preferably, the cell-retaining elements and/or agent-retaining elements are designed as barbs, preferably protruding from the surface of the thread.

Preferably, the cells and/or agents may be present underneath the cell-retaining elements and/or agent-retaining elements, which preferably protrude from the surface of the thread. More specifically, the cells and/or agents may be present on surface areas, in particular cut surface areas, of the thread, which are underneath the cell-retaining elements and/or agent-retaining elements and which are preferably covered with the cell-retaining elements and/or agent-retaining elements resting against the thread's surface.

As an alternative or in combination, the cells and/or agents may be present on the lower surface (underside) of the cell-retaining elements and/or agent-retaining elements with the cell-retaining elements and/or agent-retaining elements preferably protruding from the surface of the thread.

Advantageously, the cells and/or agents are clamped or lodged between the cell-retaining elements and/or agent-retaining elements and surface areas, in particular cut surface areas, of the thread, which are underneath the cell-retaining elements and/or agent-retaining elements and which are preferably covered with the cell-retaining elements and/or agent-retaining elements resting against the thread's surface. Thus, the risk of a cellular loss and/or loss of agents during implantation of the thread and, if appropriate, during an initial wound healing may be effectively minimized.

More specifically, the cells and/or agents may be attached to the cell-retaining elements and/or agent-retaining elements and/or surface areas, in particular cut surface areas, of the thread, which are preferably underneath the cell-retaining elements and/or agent-retaining elements.

In a porous thread, the cells and/or agents may also be present within the cell-retaining elements and/or agent-retaining elements.

Especially preferably, the cells and/or agents predominantly, in particular merely, colonize or occupy, in particular layer or coat, the cell-retaining structure and/or agent-retaining structure, preferably cell-retaining elements and/or agent-retaining elements thereof.

Further, the cell-retaining structure and/or agent-retaining structure, in particular cell-retaining elements and/or agent-retaining elements thereof, may be formed by injection molding, extruding, stamping, pressing, cutting, laser, and the like. Preferably, the cell-retaining structure and/or agent-retaining structure are formed by cuts made into the thread. More preferably, the cell-retaining elements and/or agent-retaining elements are designed as cuts into the thread.

Advantageously, the cell-retaining structure may also serve as agent-retaining structure and vice versa. Further, the cell-retaining elements may also serve as agent-retaining elements and vice versa.

The term "cells" encompasses at least one single cell. Preferably, the term "cells" encompasses a plurality of cells, i.e., at least two cells. More preferably, the term "cells" means a population of cells.

The term "agents" encompasses at least one single agent. Preferably, the term "agent" encompasses a plurality of agents, i.e., at least two agents. Moreover, the term "agents" may refer to a combination of different agents.

The cells may form a homogeneous or heterogeneous population. Having regard to the different characteristics of different cell types, it may be preferable that the cells are present as a heterogeneous population. Thus, the thread may advantageously be equipped or finished with different cellular characteristics.

Preferably, the thread is loaded, in particular inoculated, with the cells.

Typically, the cells are viable or living cells.

Generally, the cells may be autologous, alogenic, and/or xenogenic cells. However, to minimize the risk of immunological responses, it is especially preferred to use cells of autologous origin. To equip the thread with autologous cells, the cells are typically harvested from a patient to be treated.

Preferably, the cells are somatic cells, in particular stromal cells, i.e., connective tissue cells. More preferably, the cells are derived from epithelial tissue, endothelial tissue, adipose tissue, chondral tissue, osseous tissue, cellular lineages, and combinations thereof.

Preferably, the cells are stem cells, in particular mesenchymal stem cells. In principle, the cells may be embryonic and/or adult stem cells. However, to meet ethic concerns, adult stem cells may be preferred and embryonic stem cells may be preferably excluded.

Preferably, the cells are pluripotent stem cells. The term "pluripotent stem cells" relates to stem cells that are able to differentiate a variety of tissues.

Further preferably, the cells are omnipotent (totipotent) stem cells. The term "omnipotent stem cells" refers to cells that are able to differentiate any kind of tissue.

Preferably, the stem cells are derived from adipose tissue, in particular liposuctioned fat, bone marrow, blood, dental pulp, cornea, undifferentiated cell lineages such as undifferentiated fibroblasts, and combinations thereof. Especially preferred are adipose tissue-derived mesenchymal stem cells, due to their easy obtention (either from liposuction or lipectomy), a low donor-site morbidity and a high cell yield.

The cells may be engineered, in particular genetically engineered, cells. By way of example, the cells may be engineered to express characteristics of other cell types that may be preferably selected from the group consisting of epithelial cells, endothelial cells, chondrocytes, osteocytes, fibroblasts, adipocytes, miocytes, neurons, astrocytes, oligodentrocytes, hepatocytes, pancreatic cells, progenitor cells thereof, stem cells thereof, and combinations thereof.

More specifically, the cells may be engineered to secrete factors such as cellular and/or synthetic factors. The factors may be selected from the group consisting of antimicrobial, in particular antibiotic, factors, disinfecting factors, anti-inflammatory factors, wound healing promoting factors, cellular growth factors, morphogenetic factors, cytokines, peptides, proteins, extracellular components, cellular differentiating factors, cellular adhesion factors, cellular recruiting factors, anesthetic factors, and combinations thereof.

Useful growth factors may be selected from the group consisting of fibroblast growth factor (FGF), transforming growth factor (TGF), platelet derived growth factor (PDGF), epidermal growth factor (EGF), granulocyte-macrophage colony stimulation factor (GMCSF), vascular endothelial growth factor (VEGF), insulin-like growth factor (IGF), hepatocyte growth factor (HGF), interleukin-1B (IL-1B), interleukin-8 (IL-8), nerve growth factor (NGF), and combinations thereof.

Useful extracellular components may be selected from the group consisting of collagen, reticulin, elastin, vitronectin, fibronectin, laminin, mucopolysaccharides such as hyaluronic acid, salts thereof, and combinations thereof.

Useful cellular adhesion factors may be peptides having an amino acid sequence comprising arginine, glycine and aspartic acid.

Further, the cells may be engineered, in particular genetically engineered, to carry medicinal or pharmaceutical, in particular therapeutic, agents such as chemotherapeutic agents and/or radiotherapeutic agents. Useful agents may be selected from the group consisting of cisplatin, carboplatin, paclitaxel, Iridium-192, Iodine-125, and combinations thereof.

Especially preferably, the cells are selected from the group consisting of epithelial cells, endothelial cells, chondrocytes, osteocytes, fibroblasts, adipocytes, miocytes, neurons, astrocytes, oligodentrocytes, hepatocytes, pancreatic cells, progenitor cells thereof, stem cells thereof, engineered, in particular genetically engineered, cells thereof, and combinations thereof.

The thread may comprise a coating, preferably a coating that facilitates, enforces and/or enhances adherence of the cells. By way of example, the coating material may be selected from the group consisting of peptides, extracellular matrix proteins, in particular from eukaryote cells, antibodies, protein antigens, sugars, lipids, and combinations thereof. Useful peptides may be peptides having an amino acid sequence comprising arginine, glycine and aspartic acid. Useful extracellular proteins are selected from the group consisting of collagen, vitronectin, fibronectins, laminins, salts thereof, and combinations thereof. For coating, the thread may be, by way of example, soaked or immersed into a broth of the coating material.

The thread may comprise a porous coating, particularly in the form of a foam. Such a coating beneficially enlarges the surface of the thread which allows more cells and/or agents to be adhered thereto. More specifically, the thread may comprise cell-retaining elements and/or agent-retaining elements that are present as cuts into the coating. Thus, the cut in coating may advantageously serve as anchoring means and the pores may advantageously retain the cells and/or agents. A coating as described in this paragraph may be applied onto the thread by means of sheath extrusion, for example.

As already mentioned, the thread may comprise agents, in particular factors, additionally or alternatively to cells. More specifically, the thread may be equipped or finished, in particular loaded, with agents. This is particularly useful to confer the thread desired characteristics, in particular in view of therapeutic terms. Useful agents may be agents that foster cellular colonization of the thread. Further, useful agents may be agents that induce differentiation of stem cells and/or expression of cellular characteristics such as secretion of desired substances, for example, peptides, proteins, cytokines, and the like.

Preferably, useful agents are factors that are selected from the group consisting of antimicrobial, in particular antibiotic, factors, disinfecting factors, anti-inflammatory factors, wound healing promoting factors, cellular growth factors, morphogenetic factors, cytokines, peptides, proteins, extracellular components, cellular differentiating factors, cellular adhesion factors, cellular recruiting factors, anesthetic factors, and combinations thereof.

Useful growth factors may be selected from the group consisting of fibroblast growth factor (FGF), transforming growth factor (TGF), platelet derived growth factor (PDGF), epidermal growth factor (EGF), granulocyte-macrophage colony stimulation factor (GMCSF), vascular endothelial growth factor (VEGF), insulin-like growth factor (IGF), hepatocyte growth factor (HGF), interleukin-1B (IL-1B), interleukin-8 (IL-8), nerve growth factor (NGF), and combinations thereof.

Useful extracellular components may be selected from the group consisting of collagen, reticulin, elastin, vitronectin, fibronectin, laminin, mucopolysaccharides such as hyaluronic acid, salts thereof and combinations thereof.

Useful cellular adhesion factors may be peptides having an amino acid sequence comprising arginine, glycine and aspartic acid The agents may be medicinal or pharmaceutical, particularly therapeutic, agents. Useful agents may be chemotherapeutic agents and/or radiotherapeutic agents, in particular selected from the group consisting of cisplatin, carboplatin, paclitaxel, Iridium-192, Iodine-125, and combinations thereof.

The thread may be designed as an absorbable, partially absorbable or non-absorbable thread. Further, the thread may be a natural or synthetic thread.

Preferably, the thread is made of a non-absorbable material that is preferably selected from the group consisting of polyolefine such as polyethylene, polypropylene, polyvinylidene difluoride (PVDF), polytetrafluoroethylene (PTFE), in particular expanded polytetrafluoroethylene (ePTFE), polytetrafluoropropylene or polyhexafluoropropylene, polyester such as polyethylene terephthalate, polypropylene terephthalate or polybutylene terephthalate, polyamide such as Nylon 6 or Nylon 6.6, polyurethane, silk, cotton, copolymers thereof and combinations thereof. Especially preferred is Nylon, silk, polyester, cotton or a mixture of polyester and cotton.

More specifically the thread may be made of a polyethylene selected from the group consisting of low-density polyethylene (LDPE), high-density polyethylene (HDPE), high-molecular-weight polyethylene (HMWPE), ultra-high-molecular-weight polyethylene (UHMWPE), and combinations thereof.

Further preferably, the thread may be made of an absorbable material such as a polyhydroxyalkanoate. More specifically, the thread may be made of an absorbable material that is preferably selected from the group consisting of polyglycolide, polylactide, poly-ε-caprolactone, polytrimethylene carbonate, polyparadioxanone, poly-3-hydroxybutyrate, poly-4-hydroxybutyrate, copolymers thereof and combinations thereof. A preferred copolymer is made of glycolide and lactide, in particular in a weight ratio from 9:1 to 1:9. A further preferred copolymer is made of glycolide and ε-caprolactone.

The term "copolymer" is preferably understood as a polymer that is composed of at least two different monomer units. Thus, tripolymers, tetrapolymers, and the like may also be encompassed by the term "copolymer". More specifically, a copolymer may be present as a random copolymer, alternating copolymer, block or segmented copolymer or graft copolymer. Further, the copolymer may have an isotactic, syndiotactic or atactic structure.

Further preferably, the thread is designed as a fiber or monofilament, pseudo monofilament or multifilament. More specifically, the thread may be designed as a braided or twisted thread. A pseudo monofilament is preferably to be understood as multifilament covered by a sheath, coating, wrapping, and the like.

Further, the thread may be present in an undrawn or drawn state. However, in view of mechanical stability, in particular tensile strength, of the thread, it is advantageous that the thread is designed as a drawn thread. In this regard, it may be advantageously that the thread comprises cell-retaining elements and/or agent-retaining elements, which are formed, in particular cut, into the thread when the thread is present in an undrawn state, wherein the thread is drawn after forming the cell-retaining elements and/or agent-retaining elements. In other words, the thread may be obtained or obtainable by a method comprising the steps of:

a) forming, in particular cutting, cell-retaining elements and/or agent-retaining elements into an undrawn thread, and b) drawing the thread.

Further, the thread may be present as a thread having a core-sheath-structure. In this regard, the cell-retaining structure and/or agent-retaining structure, in particular cell-retaining elements and/or agent-retaining elements thereof, are typically derived from the sheath material.

In general, the thread may be applied in various fields of medicinal, in particular surgical, application. In particular, the thread may be applied in the field of hemostasis, minimal invasive surgery, laparoscopic surgery, surgery of the gastrointestinal tract, surgery of the urogenital tract, surgery of the respiratory tract, eye surgery, vascular surgery, plastic and/or reconstructive surgery, surgery on muscle tissue, epithelial tissue, nerve tissues and/or in the field of repair of tendons, fascia, osseous tissue, connective tissue and/or cartilaginous tissue, preferably in the field of treating invertebral disc defects and/or articular cartilage defects, in particular in the field of treating meniscal cartilage defect.

Particularly preferably, the thread is designed as a filler, in particular as a surgical filler, preferably in the field of plastic and/or reconstructive surgery. More specifically, the thread may be used to fill, and thus tightening and/or smoothening, small body areas such as wrinkles and/or folds to minimize their appearance and thus contributing to a better result in view of cosmetic terms.

The cell-retaining and/or agent-retaining structures may be derived from a three-dimensional, in particular scaffold-like, structure, of the thread. For instance, the thread may be woven into a basket or tube. Such threads are particularly useful in view of filling, and thus tightening and/or smoothening larger body areas such as malar, nose, chin and/or mammary.

In principle, the thread may be inserted into the body of a patient by laparoscopic surgery, minimally invasive surgery, and the like.

The thread may be connected to a surgical instrument, preferably a surgical needle or cannula.

We also provide a surgical set comprising a thread and a surgical instrument, preferably a surgical needle or surgical cannula. The thread may be advantageously placed within or connected to the surgical instrument, when entering tissue. With respect to further details and advantages, in particular in view of the thread, reference is made in its entirety to the previous description.

Further, we provide a method for manufacturing a thread. For this purpose, a thread comprising a cell-retaining structure and/or agent-retaining structure is finished or equipped with cells and/or agents.

In general, the finishing may be performed before implantation of the thread, in particular immediately before an operation. As an alternative or in combination, the finishing may be performed after implantation of the thread.

More preferably, the thread is loaded, in particular inoculated, with the cells and/or agents.

Preferably, the thread is incubated in the presence of a culturing medium including the cells. More specifically, the thread may be immersed into a culturing medium including the cells. As an alternative, a culturing medium including the cells may be inoculated onto the thread.

To facilitate cellular colonization of the thread, the thread may be incubated in the presence of a culturing medium including the cells for 1 to 14 days, in particular 2 to 10 days, preferably 2 to 7 days.

The culturing medium may additionally include agents as described in the previous description.

After incubating, the thread may be washed, preferably to get rid of undesired components that may be in particular derived from a culturing medium.

The culturing medium may be present as a solution or suspension.

For finishing the thread with the agents, the thread may be immersed or soaked in a solution or suspension including the agents.

Especially preferably, the thread is immersed in a solution having a concentration of the cells and/or agents which are enough to cover the thread for long enough for the cells and/or agents to adsorb to the thread.

For a cellular finishing of the thread, it may generally be preferred to use a cell-containing solution or cell-containing suspension, preferably having a cell concentration of 50000 cells per ml.

Further, a cell-retaining structure and/or agent-retaining structure, in particular cell-retaining elements and/or agent-retaining elements thereof, may be coated, in particular pre-coated, with the cells and/or agents. Depending on the nature of cell-retaining elements and/or agent-retaining elements, the coating may be performed within the cell-retaining elements and/or agent-retaining elements, onto the cell-retaining elements and/or agent-retaining elements or between the cell-retaining elements and/or agent-retaining elements and surfaces of the thread, which are preferably underneath the cell-retaining elements and/or agent-retaining elements.

With respect to further details and advantages, in particular in view of the thread and the cells, reference is made in its entirety to the previous description.

We also provide a method for repairing tissue, in particular for closing wound edges, comprising the step of inserting a thread into a tissue to be repaired, in particular into wound edges to be closed.

More specifically, the thread may be inserted, advantageously by endoscopic means, into an organ, for example, to promote tissue regeneration. For this purpose, the thread preferably comprises cells engineered to secrete growth factors such as vascular growth factors aimed at promoting local vascular growth in an area that needs blood supply, such as an ischemic heart or a newly transplanted area.

The thread may be inserted into tissue to inhibit cell proliferation such as for cancer treatments. For this purpose, the thread preferably comprises stem cells that are engineered to carry a cytotoxic substance.

The thread may be inserted by a suitable surgical instrument such as a surgical needle or cannula.

Further, we also provide a method for filling a body area such as wrinkles, folds, malar, nose, chin, mammary, and the like, comprising the step of placing a thread in a body area to be filled.

The thread may be placed in the desired body area minimal invasively.

Advantageously, the cells may be induced by the administration of useful agents, particularly factors, to express desired characteristics, by way of example, to secrete therapeutic substances and/or, in case that the cells are present as stem cells, to foster their differentiation to a desired cell type. As an alternative or in combination, the thread may already be finished with useful factor and agents, respectively.

With respect to further features and advantages, in particular in view of the thread, reference is made in its entirety to the previous description.

Further features and advantages will become apparent from the following description of preferred forms and by reference to the examples and descriptions of the figures in conjunction with the features of the appended claims and the figures. Individual features can be realized either singly or severally in combination.

FIG. 1 schematically shows a thread 100. The thread 100 is preferably designed as surgical thread or surgical material and comprises a cell-retaining structure 110 and cells 120. The cell-retaining structure 110 comprises cell-retaining elements 115 in the form of depresssions. The depressions 115 are dimensioned to meet at least one cell. The cells 120 may not only colonize the depressions 115 as shown. In fact, the cells 120 may also colonize the remaining surface of the thread 100. By colonizing the depressions 115, the cells 120 are advantageeously prevented from getting lost during the implantation of the thread 100. Thus, an effective amount of the cells 120 may be delivered to tissue to be treated by the thread 100. To facilitate entrance of tissue, the thread 100 may be connected to a surgical needle 130 as shown in FIG. 1.

Figure 2:
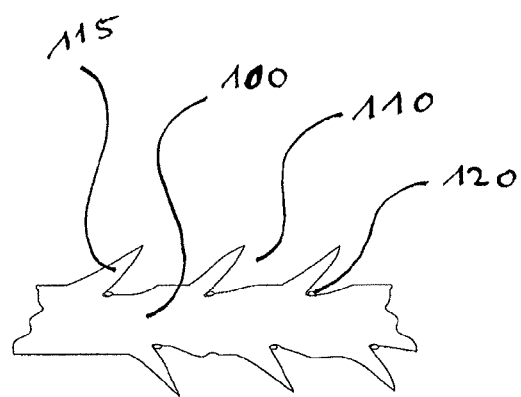
FIG. 2 schematically shows another example of the thread.

FIG. 2 schematically shows an alternative example of a thread 100. The thread 100 comprises a cell-retaining structure 110 having cell-retaining elements 115 in the form of protuberances, preferably in the form of barbs. Advantageously, the cells 120 may be lodged between the protuberances 115 and thread surface areas 108 underneath the protuberances 115. Thus, the risk of a cellular loss, in particular by peeling off the cells 120, during insertion of the thread 100 may be effectively minimized.

The threads 100 as depicted in FIGS. 1 and 2 are especially useful as surgical fillers, in particular to fill small body areas. Thus, the thread 100 may be applied, by way of example, in the field of plastic and/or reconstructive surgery, particularly to treat wrinkles and folds to minimize their appearance.

Figure 3:
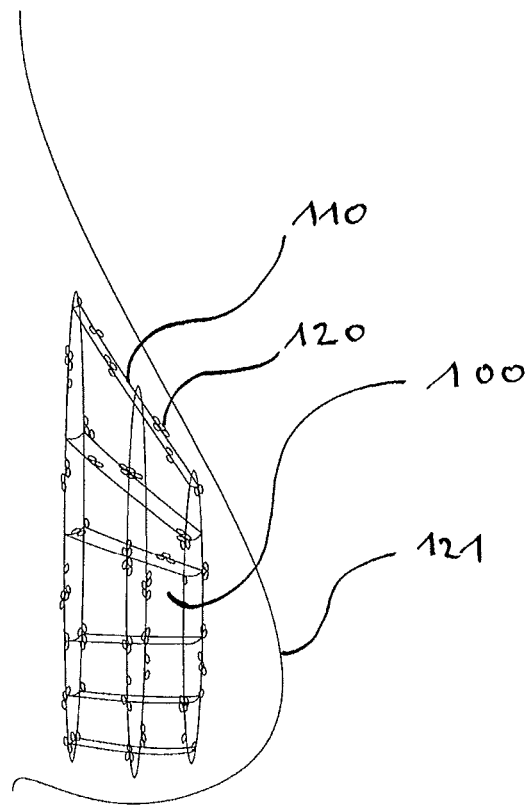
FIG. 3 schematically shows yet another example of the thread.

FIG. 3 schematically shows a further example of a thread 100. The thread 100 comprises a cell-retaining structure 110 in form of a basket-like structure which is colonized by cells 120. The thread 100 as displayed in FIG. 3 is in particular useful for filling comparatively large body areas. Thus, the basket-structured thread 100 may be, by way of example, applied to fill a body area in a female breast 121.

Figure 4:
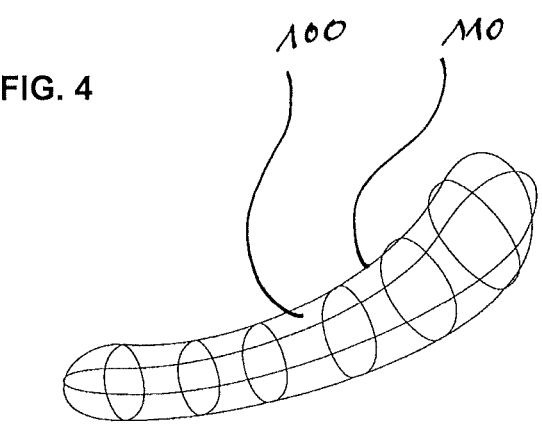
FIG. 4 schematically shows a further example of the thread.

FIG. 4 schematically displays another example of a thread 100. The thread 100 comprises a cell-retaining structure 110 in the form of a tubular-like structure and cells colonizing the tubular structure (not shown). The thread 100 is also useful as a surgical filler for comparatively large body areas such as areas around the malar bone.

EXAMPLES

1. Materials

A monofilament thread made of a copolymer made of glykolide and lactide and a monofilament thread made of Nylon (polyamide 6.6) were used.

Further, a monofilament thread made of polydioxanone (PDO) having a diameter of USP 1 was used.

Furthermore, human adult adipose tissue-derived stem cells and chondrocytes were used as cells for finishing the above mentioned threads.

2. Processing of the Threads

The thread made of the copolymer and the thread made of Nylon as recited under 1. Materials were cut in superficially by a cutting apparatus, thereby forming depressions capable of meeting cells.

The PDO-thread as recited under 1. Materials was cut in to generate barbs onto the surface of the thread.

3. Isolation and Culturing of the Cells 3.1. Isolation and culturing of adult Human Adipose Tissue-Derived Stem Cells The adipose tissue was obtained by liposuction. A cannula with a blunt end was introduced into the subcutaneous space through a small periumbilical incision (less than 0.5 cm in diameter). The suction was performed by moving the cannula along the adipose tissue compartment located under the abdominal wall, thus aiding the mechanical disruption of the adipose tissue. To minimize the loss of blood, a saline and epinephrine solution was injected as a vasoconstriction agent. 80 to 100 ml of raw lipoaspirate cells were obtained from each patient using this procedure.

The lipoaspirate was placed in a flask containing sterile phosphate buffered saline (PBS) at pH 7.4 and 4° C. The resulting mixture was weighed using a precision scale. Afterwards, it was taken to a biological exposure chamber to be processed.

The adipose tissue was washed with PBS until all visible blood and aspirated liquids were eliminated. The step facilitated a more selective cell isolation, with less erythrocytes and debris, since the presence of these elements impaired subsequent steps in the process of isolating the adipose tissue-derived stem cells.

The remaining tissue was placed in a container and then stirred (using a magnetic stirrer) for 60 minutes at 37° C. After that, it was submitted to enzymatic digestion.

For enzymatic digestion, the following compounds (per gram of tissue) were used: 2 ml Dulbecco's Modified Eagle Medium (DMEM), 2 mg/ml Collagenase A, 20 mg/ml Bovine Serum Albumin (BSA)—Fraction V, 124 μg/ml penicillin and 100 μg/ml streptomycin.

After 60 minutes, the digestion was interrupted by the addition of Fetal Bovine Serum, in a proportion equal to 10% of the total volume of the enzymatic solution. This inactivation of Collagenase was important to prevent cell lysis.

The digested material was transferred to a Falcon tube and centrifuged at 200×g for 5 minutes.

After centrifugation, the floating fraction (which contained the adipocyte fraction) was discarded, and the pellet containing the stromal vascular fraction (SVF) was resuspended in a mixture of DMEM, 10% FBS, 124 μg/ml penicillin and 100 μg/ml streptomycin.

The collected cells were placed in a 25 cm$^2$ culture bottle containing DMEM, 10% FBS, 124 μg/ml penicillin and 100 μg/ml streptomycin. This mixture prevented bacterial contamination in the cell culture.

The culture bottles were left in an incubator at a concentration of 5% carbon dioxide and 37° C. to promote cell expansion.

During the first two days, the bottles were washed with PBS to remove debris, erythrocytes and other non-adherent cells (stem cells adhered to the bottom of the culture bottle, thus not being removed by the wash). By the end of this step, the resulting culture was almost exclusively constituted by adipose tissue-derived stem cells.

Once, the adipose tissue-derived stem cells were adequately isolated, the culture medium was changed on alternate days. Thus, the cells expanded and reached about 70% confluence (which means cells grouped together and occupied about 70% of the inner bottom surface of the culture bottle).

In this primary culture, once the cells reached the expected confluence, they were submitted to trypsinization (trypsin is a serine protease which was used to destroy the proteins that facilitate adhesion to the bottle and intercellularly), using 5 ml Trypsin-EDTA, thus forming a cell suspension.

That suspension was used to transfer cells to a larger bottle (75 cm$^2$), with the purpose of increasing cell numbers.

Using the above described technique, around 1,000,000, adipose tissue-derived stem cells were obtained in 15 days, starting from 10 g of adipose tissue extract.

3.2 Isolation and Culturing of Chondrocytes

A cartilage biopsy was harvested arthroscopically from a patient's knee and transferred into a sterile flask containing a "transport medium" (DMEM/F12 with 20% fetal calf serum). The flask containing the transport medium was delivered within 48 hours to the cell culturing laboratory, where the mixture was weighed using a precision scale and subsequently was taken to a biological exposure chamber to be processed.

The chondrocytes were expanded in tissue culture flasks in a $CO_2$ incubator (5% $CO_2$) at 37° C. in growth medium for 3 to 6 weeks and later on maintained in DMEM/F12 with the patient's (mammal) own heat inactivated serum (range 10 to 20%) for 3 to 10 days. The aforementioned growth medium was supplemented with L-ascorbic acid (50 μg/ml (300 μmol/l)), gentamicin sulfate (50 μg/ml (10 mmol/l)) and Fungizone (2 μg/ml (2.2 μmol/l)). When the chondrocyte culture had been expanded to the amount of cells needed for the repair of a cartilage lesion of a given patient (mammal), the cells were harvested by trypsinization in 0.25% trypsin in 1 mM EDTA, washed in medium containing fetal calf serum (20%) and centrifuged at 900×g for 10 minutes at room temperature, and resuspended to cell numbers between 0.5 to 2×10$^6$ cells per 0.1 ml growth medium (5 to 20×10$^6$ cells per 1 ml growth medium). The optimum cell count per 0.1 ml growth medium for implantation was around 1 million cells. In general, a cartilage defect has room for 0.1 ml cell suspension per 1 cm$^2$ defect.

4. Cellular Finishing of the Threads 4.1 Finishing of the Threads with Adipose Tissue-Derived Stem Cells The different thread types as recited under 1. Materials were cut into fragments having a length of approximately 1 cm. Afterwards, the thread fragments were deposited onto wells of a 12 well-plate. A suspension of adipose tissue-derived stem cells was prepared in a concentration of around 50,000 cells per ml and 1 ml of the suspension was added to each well. The culturing dishes onto which the thread fragments were deposited were cultured in the presence of the cellular suspension in an atmosphere with 5% $CO_2$ at 37° C. for 24 hours.

Afterwards, the thread fragments were taken out of the wells and subsequently placed in wells containing a DAPI (4',6-diamidino-2-phenylindole)/methanol-solution. DAPI is a fluorescent dye that specifically binds to DNA, thereby forming strong fluorescent DNA-DAPI-complexes. DAPI is rapidly incorporated into cells resulting in strong fluorescent cellular nuclei, which may be detected by means of cytoplasmatic fluorescence.

The thread fragments were incubated in the presence of DAPI/methanol for 15 minutes at 37° C. After incubation, the thread fragments were investigated under an electron microscope, thereby confirming a cellular colonization of the thread fragments. In particular, it turned out that also the depressions and barbs of the threads were populated by the adipose-tissue derived stem cells.

4.2 Finishing of the Threads with Chondrocytes

The different thread types as recited under 1. Materials were cut into fragments having a length of approximately 1 cm. Afterwards, the thread fragments were deposited onto wells of a 12 well-plate. A suspension of chondrocytes was prepared in a concentration of around 1 million cells per ml and 1 ml of the suspension was added to each well. The culturing dishes onto which the thread fragments were deposited were cultured in the presence of the cellular suspension in an atmosphere with 5% $CO_2$ at 37° C. for 24 hours.

Afterwards, the thread fragments were taken out of the wells and subsequently placed in wells containing DAPI/methanol-solution. The thread fragments were incubated in the presence of DAPI/methanol for 15 minutes at 37° C. After incubation, the thread fragments were investigated under an electron microscope, thereby confirming a cellular colonization of the thread fragments. In particular, it turned out that also the depressions and barbs of the thread fragments were populated by the chondrocytes.

The invention claimed is:

1. A surgical thread comprising a cell-retaining structure and cells, wherein the cell-retaining structure comprises cell-retaining elements which protrude from a surface of the thread, the thread is only partially colonized by the cells, and the cells are clamped between the cell-retaining elements and thread surface areas underneath the cell-retaining elements.

2. The thread according to claim 1, wherein the cell-retaining elements are protuberances.

3. The thread according to claim 1, wherein the cell-retaining elements are derived from fibers which contribute to the textile structure of the thread.

4. The thread according to claim 1, wherein the cell-retaining elements are barbs protruding from the surface of the thread.

5. The thread according to claim 1, wherein the cells predominantly colonize the cell-retaining structure, in particular cell-retaining elements thereof.

6. The thread according to claim 1, wherein the cells are of autologous, alogenic, and/or xenogenic origin.

7. The thread according to claim 1, wherein the cells are stromal cells derived from epithelial tissue, endothelial tissue, adipose tissue, chondral tissue, osseous tissue, cornea, dental pulp, bone marrow, blood, cellular lineages, or combinations thereof.

8. The thread according to claim 1, wherein the cells are adult mesenchymal stem cells.

9. The thread according to claim 8, wherein the stem cells are derived from liposuctioned fat, bone marrow, blood, cornea, dental pulp and/or undifferentiated cell lineages and undifferentiated fibroblasts.

10. The thread according to claim 1, wherein the cells are selected from the group consisting of epithelial cells, endothelial cells, chondrocytes, osteocytes, fibroblasts, adipocytes, miocytes, neurons, astrocytes, oligodentrocytes, hepatocytes, pancreatic cells, progenitor cells thereof, stem cells thereof, genetically engineered cells thereof, and combinations thereof.

11. The thread according to claim 1, wherein the thread is equipped with factors selected from the group consisting of antimicrobial, in particular antibiotic, factors, disinfecting factors, anti-inflammatory factors, wound healing promoting factors, cellular growth factors, cellular differentiating factors, cellular adhesion factors, cellular recruiting factors, anesthetic factors, cytokines, extracellular components and combinations thereof.

12. The thread according to claim 1, wherein the thread is a monofilament, pseudomonofilament or multfilament or a braided or twisted multifilament.

13. The thread according to claim 1, wherein the thread is made of a non-absorbable material selected from the group consisting of polyolefin, polyethylene, polypropylene, polyvinylidene difluoride, polytetrafluoroethylene, expanded polytetrafluoroethylene, polytetrafluoropropylene, polyhexafluoropropylene, polyester, polyethylene terephthalate, polypropylene terephthalate or polybutylene terephthalate, polyamide, Nylon 6, Nylon 6.6, polyurethane, silk, cotton, copolymers thereof, and combinations thereof.

14. The thread according to claim 1, wherein the thread is made of an absorbable material selected from the group consisting of polyglycolide, polylactide, poly-ϵ-caprolactone, polytrimethylene carbonate, polyparadioxanone, poly-3-hydroxybutyrate, poly-4-hydroxybutyrate, copolymers thereof, and combinations thereof.

15. A surgical filler for plastic surgery and/or reconstructive surgery that minimizes appearance of wrinkles and/or folds comprising the thread according to claim 1.

16. A surgical set comprising at least one surgical instrument and a thread according to claim 1.

17. A method for manufacturing a surgical thread according to claim 1, comprising finishing a thread comprising a cell-retaining structure with cells.

18. The method according to claim 17, wherein the thread is incubated in the presence of a culturing medium including the cells.

19. The method according to claim 17, wherein the thread is immersed in a culturing medium including the cells.

20. The method according to claim 17, wherein a culturing medium including the cells is inoculated onto the thread.

* * * * *